United States Patent [19]

Prey

[11] 3,956,278

[45] May 11, 1976

[54] NOVEL MIXED PARTIAL ESTERS OF CARBOHYDRATES

[75] Inventor: Vinzenz Prey, Vienna, Austria

[73] Assignee: Krems-Chemie Gesellschaft m.b.H., Krems, Austria

[22] Filed: Nov. 5, 1973

[21] Appl. No.: 412,831

[52] U.S. Cl. ............................. 260/234 R; 424/180
[51] Int. Cl.$^2$ ......................................... C08B 37/00
[58] Field of Search ................................ 260/234 R

[56] References Cited
UNITED STATES PATENTS

| | | | |
|---|---|---|---|
| 3,257,827 | 5/1966 | Schnell et al. | 260/234 R |
| 3,378,544 | 4/1968 | O'Boyle | 260/234 R |
| 3,558,597 | 1/1971 | Brachel et al. | 260/234 R |
| 3,655,645 | 4/1972 | Jacques | 260/234 R |

*Primary Examiner*—Johnnie R. Brown
*Assistant Examiner*—Cary Owens

[57] ABSTRACT

Novel mixed partial esters of certain carbohydrates and sugars are prepared by reacting the carbohydrate starting material with an aliphatic acylation agent having up to two carbon atoms in the chain until the resulting product has an acylation number of up to one acyl group per monose unit, and then reacting the mixture with a higher fatty acid reactant having at least six carbon atoms in the chain in the presence of an acid catalyst. The acylation agent and fatty acid reactant may be in the form of the free acid or the anhydride, examples of both being disclosed, and the carbohydrate starting material may be present in aqueous solution or suspension. The novel esters, which may contain 7 or more % of combined higher fatty acid have desirable interfacial properties and are biodegradable.

17 Claims, No Drawings

NOVEL MIXED PARTIAL ESTERS OF CARBOHYDRATES

BACKGROUND OF THE INVENTION

This invention relates to a process for the preparation of mixed partial esters of carbohydrates, particularly of monoses or oligosaccharides or their cleavage products, and hydrolysis products of polysaccharides.

It is an object of the invention to produce interfacially-active substances from readily accessible starting materials by a simple process requiring little technical or economic outlay, and at the same time to obtain products, which after use, can be completely degraded biologically.

It has been proposed to produce partially acetylated saccharides having on average 5 acetyl groups per molecule in aqueous solution by means of an organic extraction agent, the resulting products being satisfactorily interfacially-active It is an object of the invention to produce still lower-acylated carbohydrates which are modified by the introduction of fatty acid radicals and which are particularly suitable as detergent substances. Exhaustive tests have shown that novel interfacially-active mixed partial esters can be obtained without the additional use of organic solvents by a very simple process.

Individual mixed esters of sugars with higher and lower fatty acids which can be obtained by esterification of a carbohydrate-containing starting material with higher and lower fatty acids or fatty acid anhydrides in the presence of acid catalysts are known per se, but these mixed esters are completely or highly esterified carbohydrates the special properties of which (resistance to heat and hydrolysis, water-repellent action) make them suitable as plasticizers, film-forming agents, waterproofing agents or oil additives in internal combustion engines, but not as interfacially-active agents.

In contradistinction to this, a feature of the present invention is the preparation of only low-acylated mixed esters of the said carbohydrates having outstanding interfacially-active properties. In this connection it was found that the conversion of the carbohydrate starting material to an ester having only a low acyl number produces a product which, together with a lower-aliphatic acylation agent, serves as a solvent both for the carbohydrate starting material and for a higher fatty acid component. A prerequisite to this double function is that, for example, in the case of saccharose, acylation with the lower-aliphatic acylation agent should be carried out only to a low acylation number, usually a maximum of one hydroxyl group out of the three primary hydroxyl groups, for the esterification with the lower-aliphatic acylation agent, so that there remains a maximum of two hydroxyl groups available for the esterification with the higher fatty acid radical.

SUMMARY OF THE INVENTION

Accordingly, the present invention provides a process for the preparation of a mixed partial ester of a carbohydrate selected from monoses, oligosaccharides and cleavage products thereof, and hydrolysis products of polysaccharides, wherein the carbohydrate is reacted with an aliphatic acylation agent having up to two carbon atoms in the chain until the resulting product has an acylation number of a maximum of one acyl group per monose unit, and wherein the resulting reaction mixture is reacted with a fatty acid or an anhydride thereof containing at least six carbon atoms in the chain in the presence of an acid catalyst, together with, where applicable, any remaining proportion of the aliphatic acylation agent which has not yet been used in the first stage.

In the present process the starting materials, i.e. carbohydrate, aliphatic acylation agent and fatty acid acylation agent (free fatty acid or fatty acid anhydride), can be brought into action successively in one and the same reaction vessel, i.e. as in a single-vessel or "economy" process. This eliminates the need for separate production and separation of a partially acylated carbohydrate as required in a previously proposed process and the difficulties bound up with the possible use of an organic solvent are obviated. The reaction of the starting components in a single step taking place in the same reaction vessel also enables the yields to be improved to close to the theoretical values. The mixed esters produced by the present process have only ½ to 1 lower acyl group per molecule and need contain only 5% by weight — referred to the end product — or less of chemically combined higher fatty acid. The mixed partial esters obtainable by the present process are highly interfacially-active and have a surface tension of the order of 30 dyne/cm. and an immersion wetting property (stationary) of the order of 1 to 2 min., and are therefore excellent detergent substances. Compared with interfacially-active esters of saccharose with higher fatty acids without lower-aliphatic acyl radicals and inadequate immersion wetting power and a high fatty acid proportion, for example, 41% palmitic acid in the case of saccharose monopalmitate as detergent substance, a much lower proportion, for example, 5% of chemically combined higher fatty acid, is sufficient to provide a better action for the present ester than the said saccharose monopalmitate.

It has been found particularly advantageous to carry out the partial esterification reaction with the higher fatty acid or an anhydride thereof until a chemically combined acid content of 4 to 5% is obtained. However, the invention is not confined to compliance with this range, because the favourable effects of the said mixed esters can also be obtained with less than 4% chemically combined higher fatty acid, and with higher proportions, for example 7% or more, of fatty acid radicals containing at least six carbon atoms in the chain.

DESCRIPTION OF PREFERRED EMBOIMENTS

In a preferred embodiment of carrying out the present process, the carbohydrate starting material is initially reacted only with some of the aliphatic acylation agent, and then the reaction is completed with the remainder of the acylation agent together with the fatty acid or fatty acid anhydride in the presence of the acid catalyst. In this way, the formation of a homogeneous reaction medium is greatly facilitated, and the preparation of the mixed partial ester than proceeds particularly well. The described addition of the reaction components in stages can also be carried out by first adding the total quantity of aliphatic acylation agent and adding just the fatty acid component and the acid catalyst in the second stage. Whether the aliphatic acylation agent is added completely or partially in the first stage, the required acylation numbers can be obtained without difficulty in both variants of the reaction with the temperature appropriately maintained, whereupon the partial esterification of the partially acylated carbohydrate with the fatty acid radicals proceeds readily due to the presence of the acid catalyst.

The carbohydrates used as starting materials in the present process may be oligosaccharides, such as saccharose, other bioses or trioses, and also monoses, for example glucose or xylose, and equally good results can be obtained as, for example, in the case of disaccharides. It is also possible to use, for example, acid hydrolysis products from the cellulose industry as starting material, or hydrolysis products from the production of starch syrup. Similarly, mixtures of carbohydrates can be used successfully. For example, using a mixture of glucose and saccharose it is possible to obtain the corresponding mixed esters with the required surface-active properties.

The aliphatic acylation agent can be used both in the form of the free acid and of the anhydride, and the preferred acylation agents are acetylation agents such as acetic acid which is preferably used in its anhydrous form (glacial acetic acid) and/or as acetic anhydride.

The fatty acids containing at least six carbon atoms include acids such as lauric acid, palmitic acid, stearic acid, myristic acid, as well as the corresponding unsaturated fatty acids, although shorter-chain fatty acids which, however, have at least six carbon atoms per molecule, may be used. Sacacid acid is preferred, this being a mixture of fatty acids based on tall oil and having an average carbon number of about 18. The use of coco-fatty acid which is basically a mixture of lauric acid, myristic acid and palmitic acid, and of caproic acid, caprylic acid and capric acid, has also been found favourable. Instead of the free fatty acids, it is also possible to use the anhydrides of these acids or acid mixtures.

The acid catalyst is conveniently a proton acid or a Lewis acid, and is preferably p-toluenesulphonic acid. The presence of an acid catalyst facilitates the reaction at elevated temperature with the direct formation of the required acylated mixed ester. Other examples of suitable catalysts include zinc chloride and boric acid.

Acid ion exchangers in the H-form are also suitable acid catalysts for use in the present process and have the advantages that they are simple to use and improve the colour of the end products.

In one embodiment of the present process, the carbohydrate can be used in aqueous solution or in aqueous suspension. In this case, acetic anhydride is the preferred acylation agent since it insures a rapid and reliable acylation. On completion of the reaction, the remaining acylation agent in the form of glacial acetic acid can readily be removed by distillation. If desired, a mixture of acetic anhydride and glacial acetic acid can be used for the acetylation.

In order to produce a mixed ester of saccharose in an aqueous medium, the saccharose in a concentrated or saturated aqueous solution or as an aqueous suspension is initially partially acetylated to an acetylation number of about 0.5 using acetic acid anhydride at a temperature of at least 90°C., whereupon the reaction temperature is maintained or increased and the said solution or suspension is esterified further, to form the corresponding mixed partial ester of the saccharose, by means of sacacid acid and the remaining quantity of acetic anhydride not required for acetylating the saccharose to said acetylation number. The acid catalyst, which is preferably p-toluenesulphonic acid, may be supplied when the sacacid acid is added.

A particularly preferred embodiment of the present process is based on the observation that it is more favourable to carry out acylation of the carbohydrate simply by dissolving it in the acylation agent under heat, and then to introduce the fatty acid component. With this procedure, the carbohydrate can be made soluble in the acylation agent by the initial acylation and hence a direct solvent is available for the resulting acylated carbohydrate independently of extraneous additives. In this preferred procedure the carbohydrate is dissolved directly in the aliphatic acylation agent to form an acylated carbohydrate having an acylation number of up to a maximum of 1, whereupon the mixed ester is then formed by reaction with said fatty acid or an anhydride thereof in the presence of the acid catalyst.

When the above-described procedure is adopted, the dissolution of saccharose in hot glacial acetic acid, for example, gives a product which contains only 0.5 acetyl groups per dextrose unit, i.e., 50% of the dextrose is unacetylated and 50% is in the form of monoacetyl dextrose. On futher reaction of this product with a fatty acid anhydride, for example lauric acid anhydride, an end product is obtained with approximately 5% chemically combined lauric acid, a surface tension of 28.7 dyne/cm., and an immersion wetting powder (stationary) of 24 sec.. If, however, the acetylation is carried out somewhat further in the first stage, a resulting monoacetyl saccharose, for example, when reacted with lauric acid anhydride gives an end product having about 4% of chemically combined lauric acid and a surface tension of 31 dyne/cm..

In this embodiment of the present process the acylation agent intended for direct dissolution of the carbohydrate material is the free acid itself, preferably acetic acid in the form of glacial acetic acid, to which acetic anhydride may be added if required to obviate an undesirable water content.

The fatty acid component may be introduced as the free fatty acid, but it is generally found more favourable to use the anhydride of a fatty acid containing at least six carbon atoms. It is preferable to use an anhydride of lauric acid, palmitic acid, stearic acid, or myristic acid, or a mixture of anhydrides derived from a mixture of fatty acids, more particularly sacacid acid or coco-fatty acid. If, for example, the anhydride of coco-fatty acid is used, the end product contains, for example 2.5% lauric acid, 1% myristic acid, 0.6% palmitic acid, and smaller quantities of caproic acid and has a surface tension of 29.4 dyne/cm..

When the present process is applied to saccharose or glucose or to a mixture of these saccharides with direct dissolution in the acylation agent, the procedure is advantageously as follows: The carbohydrate is partially acetylated by adding it to glacial acetic acid at a temperature of at least 90°C. to form a product having an acetylation number of 0.5 to 1 acetyl groups per monose unit, whereupon the reaction with the fatty acid or its anhydride in the presence of the acid catalyst is carried out at a higher temperature than the acetylation.

It has also been found advantageous if the resulting water of reaction is continuously removed if required together with the acylation agent acid. This can be done, more particularly, by distilling off, for example, with a descending condenser, suitable thermal insulation being used. In order to ensure that the resulting water of reaction is removed as far as possible, it is even better to use a water-entraining azeotrope, which is advantageously introduced when the fatty acid component is added. This enables the water to be eliminated practically completely during the reaction at temperatures so low that undesirable discoloration due to decomposition of the resulting mixed esters can be reliably avoided. Lower alkyl acetates containing two to four carbon atoms in the alkyl radical, for example ethyl acetate or isopropyl acetate, may advantageously be used as water-entraining azeotropes. The invention will now be further illustrated by the following non-limiting Examples:

EXAMPLE 1

6 kg. of glucose were dissolved in 12 kg. glacial acetic acid at 108°C. in 3 hours. The resulting solution of the partial ester in acetic acid had an acid number of 568 which, on calculation, gave 0.536 acetyl groups per glucose molecule.

8.25 kg. lauric anhydride were then added, together with p-toluenesulphonic acid as a catalyst, and the temperature was raised to 122°C., whereupon 1.18 l. of dilute acetic acid and the water formed during the reaction distilled off. The reaction, which was complete after about 3 hours, yielded a product having a surface tension of 28.9 dyne/cm. and an immersion wetting power (stationary) of 1 min. 40 sec.. The mixed ester prepared in the aforementioned manner contained 4% of chemically combined lauric acid.

If e.g. only half the acetic acid is added during the first reaction step instead of the total prescribed amount of 12 kg., and the rest of the glacial acetic acid is added during the second step together with the higher fatty acid component, the final product which is obtained, is substantially the same.

EXAMPLE 2

The method was the same as in Example 1, except that 9 kg. of lauric acid were used instead of 8.25 kg. of lauric acid anhydride. After a reaction lasting 3 hours under the conditions given in Example 1, an interfacially-active mixed ester was obtained, containing 4% of chemically combined lauric acid and having the same properties as the product in Example 1.

EXAMPLE 3

900 g. of glucose were introduced into 1.795 kg. glacial acetic acid at 110°C.. After the glucose had dissolved (within 25 minutes) the acylation number was 0.536 acetyl groups per glucose molecule. Next, 100 ml. of i-propyl acetate were added as an entraining agent, 1.35 kg. of lauric acid anhydride were added in order to introduce a fatty acid radical and p-toluene sulphonic acid was added as a catalyst. The temperature was brought to 122°C. whereupon an azeotropic mixture of i-propyl acetate, glacial acetic acid and water continuously distilled off. The reaction was complete after 3 hours. The product had an immersion wetting power of 1 min. 55 sec. and a surface tension of 29.0 dyne/cm.. It contained 4.6% of chemically combined lauric acid.

EXAMPLE 4

The method was the same as in Example 3, except that the reaction for introducing the lauric acid radical took four hours. The resulting product, which had an immersion wetting power of 1 min. 50 sec. and a surface tension of 28.8 dyne/cm., contained 7% of chemically combined lauric acid.

EXAMPLE 5

18 kg. of glucose were dissolved in 36 kg. glacial acetic acid, after which a further 36 kg. of glacial acetic acid and 18 kg. saccharose were added. After a solution had formed, the acylation number was 0.540 acetyl groups per glucose molecule. Next, 50 kg. of lauric anhydride were added, together with p-toluensulphonic acid as a catalyst, and the temperature was brought to 122°C.. During the reaction, which was complete after about 3 hours, dilute acetic acid and the water formed were distilled off. The mixed ester obtained from the mixture of glucose and saccharose contained 4% of combined lauric acid and had a surface tension of 28 dyne/cm. and an immersion wetting power of 1 min. 45 sec..

EXAMPLE 6

100 kg. of saccharose were dissolved in 15 kg. water and heated to 95° to 100°C.. Then 20 kg. of acetic anhydride were added dropwise, the temperature being maintained at about 100°C.. The resulting acylation number was 0.550 acetyl groups per glucose molecule. Then, 7 kg. of sacacid acid and 100 g. p-toluenesulphonic acid dissolved in glacial acetic acid were added dropwise. After agitation for half an hour, the glacial acetic acid (about 20 kg.) formed during the reaction was removed by vacuum distillation. The acyl derivative obtained (yield approximately 100% referred to the saccharose used) had a surface tension of 33 dyne/cm. and excellent interfacial properties. The product contained 4.8% of combined sacacid acid.

EXAMPLE 7

100 kg. of glucose were dissolved in 15 kg. water and heated to 95° to 100°C., after which 20 kg. of acetic anhydride were added dropwise, the temperature being maintained at approximately 100°C.. The resulting acylation number was 0.535. Next, 7 kg. of sacacid acid was added dropwise, together with 10 g. of p-toluenesulphonic acid dissolved in glacial acetic acid. After the reaction had continued with agitation for half an hour, the glacial acetic acid (about 20 kg.) formed during the reaction was distilled off in vacuo. The resulting mixed ester was suitable for use as a detergent and contained 4.2% of chemically combined sacacid acid.

EXAMPLE 8

20 kg. of acetic anhydride were added dropwise to a solution of 100 kg. xylose in 15 kg. water which had been heated to 95° to 100°C., the temperature being maintained at this value during the addition. The resulting acylation number of 0.6 acetyl groups per glucose molecule. Next, 7 kg. of lauric acid and 10 g. zinc chloride dissolved in glacial acetic acid were added dropwise. After the addition had ended, agitation was continued for 30 minutes, after which the glacial acetic acid formed was removed by vacuum distillation. The resulting acyl derivative of xylose had interfacial properties which were as good as those of the products described in the preceding Examples, and contained 4.1% of combined lauric acid.

EXAMPLE 9

100 kg. of a steam-treated partial hydrolysis product of wood was dissolved in 15 kg. of water at 95° to 100°C., after which 20 kg. of acetic anhydride were gradually added, the temperature being maintained at 100°C.. The acylation number was approximately the same as in the preceding Examples. Next, 7 kg. of palmitic acid and 10 g. p-toluenesulphonic acid dissolved in glacial acetic acid were added dropwise. After the addition was complete, agitation was continued for 30 minutes, after which the acetic acid formed was removed by vacuum distillaton. The resulting mixed acyl derivatives had good surface-active properties, corresponding to those of the products described in the preceding Examples. The mixed ester contained about 3.8% of chemically combined palmitic acid.

EXAMPLE 10

20 g. (0.058 mol) saccharose and 30 g. (0.5 mol) glacial acetic acid were heated to 95°C. for 10 minutes to form a solution, which became clear after 1 hour, and the solution was agitated for a further hour at 95°C.. A separate solution was prepared from 20 g. (0.12 mol) coco-fatty acid and 20.4 g. (0.2 mol) acetic anhydride by heating them to 110°C. for 10 minutes with agitation and continuing the agitation for 2 hours at the same temperature. After cooling to 70°C., the latter solution was combined, with agitation, with the solution of saccharose in glacial acetic acid, which had likewise been brought to 70°C., 3ml. of p-toluenesulphonic acid solution (0.01 g. p-TS/ml. glacial acetic acid) were added to the resulting emulsion. The temperature immediately rose to 90°C., the solution becoming clear at 80°C.. After agitation for 1 hour at 90°C., the glacial acetic acid was removed in a rotary evaporator and unconverted coco-fatty acid was extracted with petroleum ether. The resulting mixed partial ester of saccharose had an acylation number (acetyl groups per monose unit) of approximately 0.6, contained 3.1% combined fatty acids, and had a surface tension of 31.2 dyne/cm. and an immersion wetting power of 2 min. 15 sec..

EXAMPLE 11

The first step was exactly the same as in Example 10. However, the solution of higher fatty acids was prepared from 20 g. (0.12 mol) coca-fatty acid, 10 g. (0.05 mol) lauric acid and 20.4 g. (0.02 mol) acetic anhydride, the process in other respects being the same as in Example 10. After the reaction had died down between the saccharose solution in glacial acetic acid and the solution of fatty acid components and after the glacial acetic acid had evaporated, a product was obtained which had about the same acylation number, contained about 3.9% of combined fatty acids, and had a surface tension of 30.0 dyne/cm. and an immersion wetting power of 1 min. 30 sec..

EXAMPLE 12

A solution obtained by dissolving 20 g. (0.058 mol) saccharose and 30 g. (0.5 mol) acetic acid and a solution prepared from 15 g. (0.075 mol) lauric acid and 15.3 g. (0.15 mol) acetic anhydride were mixed with agitation in a reaction vessel which had been preheated to 110°C.. Next, 5 g. of a large-pored cation-exchanger in the H-form ("Amberlyst H 15" cation-exchanger made by Messrs. Rohm and Haas, U.S.A.) was added. After 3.5 minutes a clear solution was obtained at 89°C. and was agitated for a further 4.5 minutes, whereupon the temperature rose to 105°C.. The solution was immediately cooled to 60°C. and the acetic acid was removed in a rotary evaporator and unreacted lauric acid was removed with petroleum ether. The resulting partial ester had an acylation number of two acetyl groups per saccharose molecule, contained 3.6% chemically combined lauric acid, and had a surface tension of 27.4 dyne/cm. and an immersion wetting power of 1 min. 40 sec..

What is claimed is:

1. A process for the preparation of a mixed partial ester of a carbohydrate selected from the group consisting of monosaccharides, oligosaccharides and acid hydrolysis products of oligosaccharides and polysaccharides, said ester containing up to one acyl group per monose unit of aliphatic acyl groups having up to two carbon atoms in the chain and up to 75% of fatty acid moiety having at least six carbon atoms in the chain, which consists essentially of:
   a. reacting said carbohydrate with an aliphatic acylation agent having up to two carbon atoms in the chain until the resulting product has an acylation number of a maximum of one acyl group per monose unit, and
   b. reacting the reaction mixture from (a) with a higher fatty acid reactant selected from the group consisting of fatty acids having at least six carbon atoms in the chain, anhydrides of such fatty acids and mixtures thereof, in the presence of an acid catalyst selected from the group consisting of proton acids, Lewis acids and acid ion-exchangers in the H-form.

2. The process of claim 1, wherein the reaction with the higher fatty acid reactant is carried out until the content of fatty acid moiety is about 4 to about 5%.

3. The process of claim 1, wherein the aliphatic acylation agent is selected from the group consisting of acetic acid, acetic anhydride and mixtures thereof.

4. The process of claim 1, wherein the higher fatty acid reactant is selected from the group consisting of lauric acid, palmitic acid, stearic acid, myristic acid, sacacid acid, coco-fatty acid, the anhydrides of said acids, mixtures of said acids, mixtures of said anhydrides and mixtures of said acids with said anhydrides.

5. The process of claim 1, wherein the acid catalyst is p-toluenesulphonic acid.

6. The process of claim 1, wherein the carbohydrate is present in aqueous solution.

7. The process of claim 1, wherein the carbohydrate is reacted with the acylation agent in the absence of a solvent.

8. The process of claim 1, wherein a concentrated aqueous solution of a disaccharide is reacted with acetic anhydride at a temperature of at least 90°C. until an acetylation number of about 0.5 is reached, and wherein the reaction mixture at a temperature of at least 90°C. is reacted with sacacid acid and any unreacted acetic anhydride.

9. The process of claim 8, wherein the temperature during the reaction with sacacid acid is higher than during the reaction with acetic anhydride.

10. The process of claim 1, wherein the carbohydrate is dissolved in glacial acetic acid at a temperature of at least 90°C. until an acylation number of 0.5 to 1 is reached, and wherein the reaction mixture is then reacted with said higher fatty acid reactant at a higher temperature than during the reaction with the glacial acetic acid.

11. The process of claim 10, wherein the carbohydrate is selected from the group consisting of saccharose, gluclose and mixtures thereof.

12. The process of claim 1, wherein the water of reaction is removed continuously by distillation.

13. The process of claim 12, wherein the water is removed with the aid of an azeotrope.

14. The process of claim 13, wherein the azeotrope is a lower alkyl acetate.

15. A mixed partial ester of a carbohydrate selected from the group consisting of monosaccharides, oligosaccharides and acid hydrolysis products of oligosaccharides and polysaccharides, said ester containing up to one acyl group per monose unit of aliphatic acyl groups having up to two carbon atoms in the chain and up to 75% of fatty acid moiety having at least six carbon atoms in the chain.

16. The process of claim 1, wherein the carbohydrate is selected from the group consisting of glucose, xylose, saccharose and mixtures thereof.

17. The mixed partial ester of claim 15, wherein the carbohydrate is selected from the group consisting of glucose, xylose, saccharose and mixtures thereof.

* * * * *

UNITED STATES PATENT OFFICE
CERTIFICATE OF CORRECTION

PATENT NO. : 3,956,278
DATED : May 11, 1976
INVENTOR(S) : Vinzenz Prey

It is certified that error appears in the above-identified patent and that said Letters Patent are hereby corrected as shown below:

On the Title Page, Item [30] should read:

November 6, 1972    Austria................A 9405/72

Signed and Sealed this

Seventh Day of December 1976

[SEAL]

Attest:

RUTH C. MASON
*Attesting Officer*

C. MARSHALL DANN
*Commissioner of Patents and Trademarks*